United States Patent
Safarevich et al.

(10) Patent No.: US 6,373,024 B1
(45) Date of Patent: Apr. 16, 2002

(54) LASER-WELDED JOINT

(75) Inventors: Sergey Safarevich, Valencia; Stephen M. Jones, Saugus, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/250,796

(22) Filed: Feb. 17, 1999

(51) Int. Cl.[7] .......................... B23K 26/00; A61N 1/18; A61N 1/00
(52) U.S. Cl. ..................... 219/121.64; 607/37; 607/122
(58) Field of Search ...................... 219/121.64; 29/869; 607/37, 122

(56) References Cited

U.S. PATENT DOCUMENTS

| | | | |
|---|---|---|---|
| 4,282,885 A | * 8/1981 | Bisping | 128/785 |
| 4,538,623 A | * 9/1985 | Proctor et al. | 128/784 |
| 4,566,467 A | * 1/1986 | DeHaan | 128/784 |
| 4,711,027 A | * 12/1987 | Harris | 29/869 |
| 4,953,564 A | 9/1990 | Berthelsen | 128/784 |
| 5,007,435 A | * 4/1991 | Doan et al. | 128/784 |
| 5,020,545 A | * 6/1991 | Soukup | 128/785 |
| 5,115,818 A | * 5/1992 | Holleman et al. | 128/784 |
| 5,222,506 A | * 6/1993 | Patrick et al. | 128/784 |
| 5,253,653 A | * 10/1993 | Daigle et al. | 128/772 |
| 5,324,312 A | * 6/1994 | Stokes et al. | 607/37 |
| 5,378,855 A | * 1/1995 | Delalle | 174/87 |
| 5,385,578 A | 1/1995 | Bush et al. | 607/122 |
| 5,488,768 A | * 2/1996 | Mar | 29/860 |
| 5,507,787 A | * 4/1996 | Borghi | 607/37 |
| 5,522,872 A | * 6/1996 | Hoff | 607/119 |
| 5,522,874 A | * 6/1996 | Gates | 607/127 |
| 5,569,883 A | * 10/1996 | Walter et al. | 174/84 R |
| 5,571,146 A | 11/1996 | Jones et al. | 607/37 |
| 5,676,694 A | * 10/1997 | Boser et al. | 607/122 |
| 5,807,144 A | * 9/1998 | Sivard | 439/816 |
| 6,061,595 A | * 5/2000 | Safarevich | 607/37 |
| 6,084,179 A | * 7/2000 | Walter et al. | 174/84 R |
| 6,141,593 A | * 10/2000 | Patag | 607/122 |
| 6,293,594 B1 | * 9/2001 | Safarevich et al. | 285/21.1 |

FOREIGN PATENT DOCUMENTS

| | | | |
|---|---|---|---|
| GB | 1434534 A | * 5/1976 | 29/869 |

* cited by examiner

*Primary Examiner*—Tom Dunn
*Assistant Examiner*—L. Edmondson

(57) ABSTRACT

A method of joining a longitudinally extending wound element, or coiled wire strand, and a mating component, or post, of a body implantable lead assembly wherein the former has a longitudinally extending interior passage and an end portion adapted to be received by the latter. In one embodiment, the post is formed with an integral collar spaced from a terminal end thereof. The wound element is placed about the receiving portion and over the terminal end of the mating component and against the collar. The components are then joined by thermally fusing them together, preferably by means of a laser. If the collar and the wound element are fabricated of the same alloy, the thickness of the collar and the diameter of the coiled wire strand are designed to be substantially equal. If the components are fabricated of dissimilar alloys, then the thickness of the collar is relatively dimensioned with respect to the diameter of the strand in proportion to the relative square roots of thermal diffusivity of the alloy of the collar and of the alloy of the coiled wire strand. In another embodiment, a ring member is placed about, and in engagement with, the receiving portion of the mating component. Then the components are joined, by thermally fusing them together, preferably by targeting a laser beam directly on the ring member, without regard to whether the components are fabricated of the same alloy or of different alloys.

17 Claims, 4 Drawing Sheets

LASER-WELDED JOINT

FIELD OF THE INVENTION

The present invention relates generally to lead assemblies for connecting implantable medical devices with selected body tissue to be stimulated by such devices, and more particularly to techniques for providing a secure electrical and mechanical connection between wound elements, such as coil conductors, and mating parts such as electrodes, sensors and the like, employed within such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bi-directional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart.

The lead further includes a proximal end having a connector pin adapted to be received by a mating socket in the pacemaker. A flexible, coiled or wound conductor surrounded by an insulating tube or sheath couples the connector pin at the proximal end with the electrode at the distal end.

When terminating a wound conductor to an associated electrical element such as a proximal end connector pin, a heart tissue stimulating electrode at the distal end of the lead, a blood oxygen sensor, or other such elements within the lead assembly, there is often no way to statistically ascertain the structural integrity of the termination. These joints must have a high degree of reliability for the implantable product to be acceptable for long term implants such as endocardial type pacing leads. In the past, the only way to verify the joint was to immobilize the mating part and pull on the wound conductor and this technique has been used as the chief test method. The major problem with this approach is that as the winding is pulled unequal tension is applied to the individual strains of the wound conductor. As increased tension is applied to the coil, often one strain breaks sooner than the others yielding erratic test results. The present invention provides an approach that overcomes this test method problem while at the same time providing a very reliable and secure connection between a wound element and a mating component.

Another problem associated with connections between wound elements and mating components in present day lead assemblies arises from the use of different alloys for the wound elements and mating components. Since dissimilar alloys have different melt temperatures and other thermal properties, such connections are difficult to weld. Moreover, as lead sizes decrease, problems of manufacturability arise. This is particularly true where crimping is employed to secure the wound component to a mating element. See, for example, U.S. Pat. No. 4,953,564, which discloses a cardiac pacing lead having an extendible fixation helix electrode that is mechanically and electrically connected to a rotatable conductor coil by squeezing the helix and coil together between a crimping sleeve and a crimping core. As the sizes of body implantable leads and their constituent parts become smaller, crimping becomes more difficult because the crimping tools cannot be made sufficiently small. Moreover, the same number of lead windings are not always subjected to the crimping action so that failure stress differs from lead to lead.

Some selective examples of the patented prior art will now be mentioned briefly. U.S. Pat. No. 5,569,883, to Walter et al., discloses laser-welding a wire coil to an intermediate ring or the like. U.S. Pat. No. 5,571,146, to Jones et al., discloses laser-welding dissimilar materials by means of an aperture within a lead. U.S. Pat. No. 5,385,578, to Bush et al., discloses laser-welding a wire coil to a sleeve.

It was with knowledge of the foregoing state of the technology that the present invention has been conceived and is now reduced to practice.

SUMMARY OF THE INVENTION

The present invention relates to a method of joining a longitudinally extending wound element, or coiled wire strand, and a mating component, or post, of a body implantable lead assembly wherein the former has a longitudinally extending interior passage and an end portion adapted to be received by the latter. In one embodiment, the post is formed with an integral collar spaced from a terminal end thereof. The wound element is placed about the receiving portion and over the terminal end of the mating component and against the collar. The components are then joined by thermally fusing them together, preferably by means of a laser. If the collar and the wound element are fabricated of the same alloy, the thickness of the collar and the diameter of the coiled wire strand are designed to be substantially equal. If the components are fabricated of dissimilar alloys, then the thickness of the collar is relatively dimensioned with respect to the diameter of the strand in proportion to the relative square roots of thermal diffusivity of the alloy of the collar and of the alloy of the coiled wire strand. In another embodiment, a ring member is placed about, and in engagement with, the receiving portion of the mating component. Then the components are joined, by thermally fusing them together, preferably by targeting a laser beam directly on the ring member, without regard to whether the components are fabricated of the same alloy or of different alloys.

As already noted, a primary purpose of the invention is to improve a laser-weld between a winding and a connector and to achieve this result, the laser beam energy should be distributed equally between the wire and the connector. The common weld joint typically comprises a winding screwed onto a cylindrical connector. The very last wind (that is, the wire ends) sets against a shoulder. The shoulder and the last wind (the wire ends) are then welded together in an appropriate manner (see FIG. 1).

However, the problems which occur when this technique is attempted are at least twofold:

(1) the connector requires more laser energy to melt than does the wire; and (2) the weld needs more melted metal to increase strength of the weld joint.

During welding, a laser beam melts both the connector and the wire (winding). The wire has less metal mass than does the connector. As such, the wire accumulates heat very quickly and the wire can melt easily. The wire melted metal spreads over the connector forming the weld spot. A lack of melted metal creates wire "neck down" and negative weld reinforcement, which reduces the strength of weld joint. The connector has much more metal mass, which means it draws the heat out of the weld region. This makes it difficult to melt the metal to fuse components together. Therefore, the connector requires more laser energy to melt than does the wire. To achieve a reliable weld, the beam energy must be specifically balanced between the connector and the wire. The proper beam targeting requires placement of the laser beam not equally on the joint such that more energy is on the shoulder side than on the wire. It is difficult for the line operator to target the laser beam on the joint properly.

A difference in material thermal properties magnifies the energy balance problem. For example, the platinum requires much more energy to melt then MP35N. If a joint consists of MP35N wire and a platinum connector it will need a greater misbalance of energy to melt the components equally. Proper beam targeting required to achieve a solid weld becomes more critical with dissimilar materials than with similar materials.

Consider now one instance of the invention when the joint is composed of components of dissimilar materials.

This initial embodiment includes a collar on the shoulder with a defined thickness. The collar thickness is related to the wire diameter, the wire and connector material thermal properties. According to the invention, the collar thickness can be determined by the equation presented below. The very last wind (wire ends) sets against the collar (see FIG. 2) and the collar and the winding (wire ends) are welded together (see FIG. 3).

A groove between the collar and the rest of the connector's shoulder creates a heat flow barrier, accumulating the heat in the collar weld area. The accumulated heat in the collar equalizes heat condition in the wire and in the collar and does not require a specific energy balance. Weld joint can be created with energy distribution between the wire and connector as 50/50.

The heat flow balance between the wire and connector can be regulated by collar thickness. Higher thermal properties of a material require a thinner collar to compensate for heat flow misbalance. The material thermal property difference of both materials is incorporated in the formula by the ratio of square roots of thermal diffusivity quantity. Thus:

$$B = \sqrt{a_{wire}} / \sqrt{a_{connector}} \times D \quad (1)$$

where B=collar thickness,

D=wire diameter, $a_{wire}$=wire material thermal diffusivity, and $a_{connector}$=connector material thermal diffusivity.

In a special instance, if the connector and the wire are made from the same material, the collar thickness should be equal to the wire diameter.

In another instance of the invention, the proposed design comprises a connector, a winding and a ring member on the connector. The ring member sits on the connector against a shoulder. The very last wind (wire ends) sets against the ring member (see FIG. 4). The ring member thickness is related to the winding and connector material thermal properties and wire diameter. The size of the ring member is selected to provide melted metal to fill gaps, cavities between wire ends and create the weld positive reinforcement. The ring member, the winding and the connector are welded together (see FIG. 5).

A main portion of the laser beam energy goes to melt the ring member. The peripheral portion of the laser beam heats the shoulder and winding to warm them up, helping the components fuse together. Additional metal for the melted ring member covers the winding and the shoulder of the connector, fusing the components together and filling cavities and gaps between the wires (see FIG. 6).

This joint configuration, namely, a ring member between the winding and connector, does not require a specific energy balance. The laser beam is targeted right in the middle of the ring member. Further, the weld joint strength is increased due to the weld positive reinforcement.

A feature of this embodiment of the invention is that the connector, the wire and the ring member can be made from the same or different materials.

The shape of the ring member can be specifically profiled to control the volume of melted metal around the weld joint. The profiled ring member covers more cavities and gaps between the wire ends than the wire ends. FIGS. 6A and 7A illustrate two examples of the ring member profiles.

A primary feature, then, of the present invention is the provision of a significantly improved technique for providing a secure electrical and mechanical connection between wound elements, such as coil conductors, and mating parts such as electrodes, sensors and the like, employed within such lead assemblies.

Another feature of the present invention is the provision of such a technique employing a laser.

Still another feature of the present invention is the provision of such a technique which can achieve a satisfactory connection whether or not the alloys of which the components are fabricated are the same or dissimilar.

Yet another feature of the present invention is the provision of a technique of joining a longitudinally extending wound element and a mating component of a body implantable lead assembly, the wound element having a longitudinally extending interior passage and an end portion adapted to be received by a portion of the mating component, the receiving portion of the mating component being configured to receive the end portion of the wound element.

Still a further feature of the present invention is the provision of such a technique which includes providing the receiving portion of the mating component with an integral collar spaced from a terminal end thereof, then placing the end portion of the wound element about the receiving portion and over the terminal end of the mating component and against the collar, and then joining the collar and the end portion of the wound element.

Still another feature of the present invention is the provision of such a technique according to which the thickness of the collar is relatively dimensioned with respect to the diameter of the strand of the wound element in proportion to the relative thermal diffusivity of the alloy of the collar and of the alloy of the coiled wire strand.

Yet a further feature of the present invention is the provision of such a technique which includes placing the end portion of the wound element about the receiving portion of the mating component, placing a ring member about, and in engagement with, the receiving portion of the of the mating component and joining the ring member, the end portion of the wound element and the receiving portion of the mating component.

Still another feature of the present invention is the provision of such a technique which includes targeting a laser beam on the ring member and thermally fusing the ring member, the end portion of the wound element and the receiving portion of the mating component.

Yet another of the present invention is the provision of such a technique wherein the ring member has inner or outer peripheral surfaces profiled to control the volume of melted, then fused, metal forming the weld joint.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Of primary concern with laser-welding of two metals is that there must exist a balance between energy to be delivered to the metal masses. Known connections between lead wire ends (usually a multifilar winding) to the shoulder of an electrode mount or connector is a circumferential weld. The problem with this type of weld is that the laser beam must heat a large mass of connector in order to obtain a satisfactory melt to heat and cause fixation of the wire ends. This technique is time consuming, has a tendency of overheating of the components being joined, particularly the wire winding, and has inconsistent results (i.e., reliability defects).

Alternately, spot welding has the advantages of less concern for overheating. However, current techniques of spot welding (for example, a weld on each wire end) have had inconsistent results. Filars do not always line up appropriately and/or don't get welded consistently. Disadvantages of this technique include misbalancing of energy; also, it is time consuming to target the energy beam at the exact locations needed.

Figure 1:
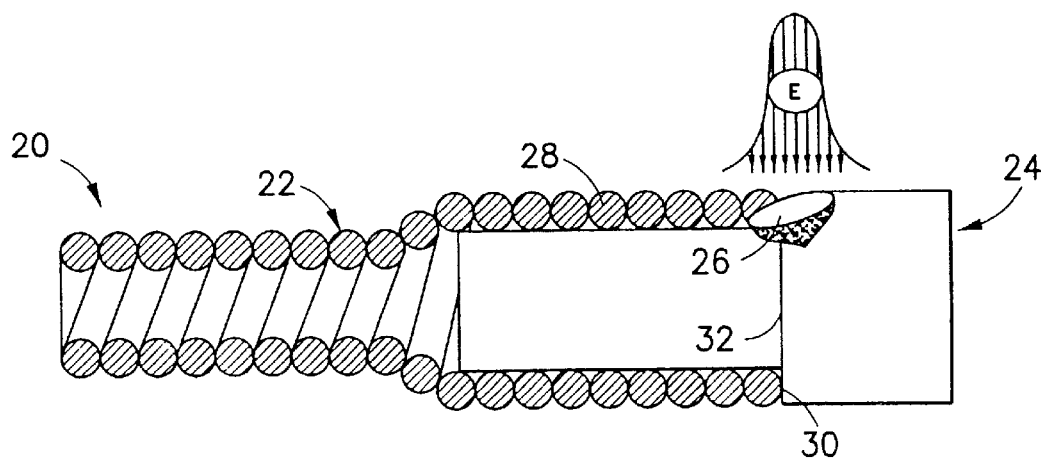
FIG. 1 is a diagrammatic side elevation view of a known laser-weld assembly between a multi wire winding and a connector.

Each of these techniques has been implemented with such inconsistent results, that throughput in production varies greatly. What is needed is a high reliability weld connection with increased manufacturability, that is, repeatability and reduced assembly time. These benefits are provided by the present invention. Turn now to the drawings and, initially, to FIG. 1 which generally illustrates a conventional circumferential laser-weld assembly 20 between a multi wire winding 22 and a connector 24. To achieve this weld assembly 20, weld spots 26 obtained by use of a laser represented by a beam E, should be distributed around the periphery of the connector to melt together each wire strand 28 and the connector 24 itself. The common weld assembly comprises the winding 22 screwed or otherwise applied onto the cylindrical connector 24. The very last wind (wire ends 30) butts up against a shoulder 32 of the connector. The shoulder 32 and the last wind (wire ends 30) are thereby welded together.

As earlier explained, the connector 24 requires more laser energy to melt than does the wire strand 28 and the weld region needs more melted metal to increase strength of the weld assembly. During welding, the laser beam E melts both the connector 24 and the winding 22. The wire possesses less metal mass than does the connector. As such, the winding accumulates heat very quickly and the wire strands 28 can melt easily. The melted metal from the winding spreads over the connector forming the weld spot 26. A lack of melted metal creates wire "neck down" and negative weld reinforcement, which reduces the strength of weld joint.

The connector has much more metal mass, which means it draws the heat out of the weld area. Unfortunately, this condition makes it difficult to melt the metal to fuse the components together. Therefore, the connector requires more energy from the laser beam E to melt than does the winding. To achieve a reliable weld, the beam energy must be specifically balanced between the connector and the winding. The proper beam targeting requires placement of the laser beam unequally on the joint such that more energy is on the shoulder side than on the wire. However, it is difficult for the assembly line operator to properly target the laser beam on the joint. A difference in material thermal properties further magnifies the energy balance problem. For example, platinum requires much more energy to melt than does MP35N, a high corrosion resistant stainless steel used for implantable devices including leads. If a joint comprises MP35N wire and a platinum connector it will need a greater misbalance of energy to melt the components equally. Proper beam targeting required to achieve a solid weld becomes more critical with dissimilar materials than with similar materials.

Figure 2:
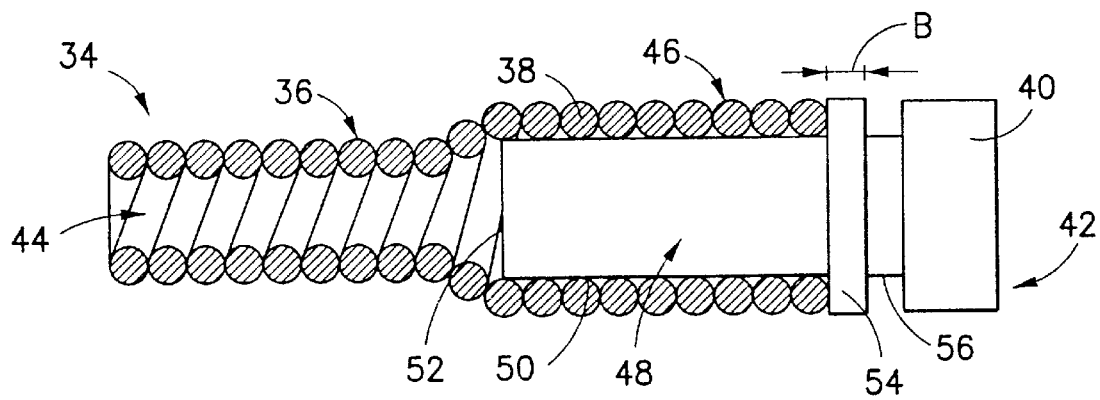
FIG. 2 is a diagrammatic side elevation view, similar to FIG. 1 but illustrating one embodiment of a laser-weld assembly embodying the invention.
Figure 3:
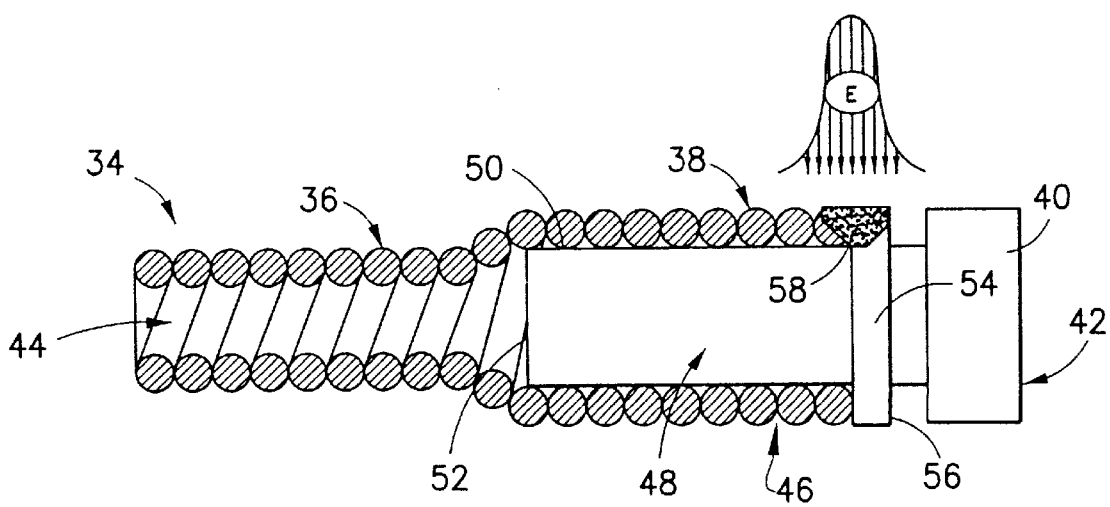
FIG. 3 is a diagrammatic side elevation view illustrating the FIG. 2 embodiment of the invention after the weld has been achieved.

For the description of a first embodiment of the invention, turn now to FIGS. 2 and 3. In this instance, a weld assembly or joint 34 serves to connect a longitudinally extending wound element 36 formed of coiled wire strands 38 and a mating connector, or component 40, of a body implantable lead assembly 42. The wound element 36 has an interior passage 44 and an end portion 46. The mating component 40 includes a post 48 for receiving the end portion 46 of the wound element 36. The post 48 has an outer surface 50, a terminal end 52, and a collar 54 which is a spaced distance from the terminal end. The end portion 46 of the wound element 36 is disposed about the post 48, over the terminal end 52, and the collar 54 and the end portion are integrally joined together in a manner to be described.

The collar 54 has a defined thickness B which is related to the wire diameter of the coiled wire strand 38 and to the material thermal properties of the wire strand and of the component 40. As earlier mentioned, the collar thickness can be described by the following formula:

$$B = \sqrt{a_{wire}}/\sqrt{a_{connector}} \times D \quad (1)$$

where B=collar thickness,

D=wire diameter, $a_{wire}$=wire material thermal diffusivity, and $a_{connector}$=connector material thermal diffusivity.

An annular groove 56 located between the collar 54 and the remainder of the component and on the side of the collar opposite the wound element 36 results in a heat flow barrier, allowing heat applies to the collar to be retained in the collar weld region. The accumulated heat in the region of the collar 54 thereby equalizes heat condition in the coiled wire strand 38 and in the collar and therefore does not require a specific energy balance. A resulting weld joint 58 can thereby be produced with energy distribution between the wire and connector as approximately 50/50.

The heat flow balance between the wire and connector can be regulated by collar thickness. Higher thermal properties of a material require a thinner collar to compensate for heat flow misbalance. The material thermal property difference of both materials is incorporated in the formula by the ratio of square roots of the value of thermal diffusivity for each material.

In the event the component 40 and the coiled wire strand 38 are made from the same material, the collar thickness should be about equal to the wire diameter. It is a common practice to construct the weld assembly 34 such that the receiving portion, or post 48, of the component 40 is cylindrical and has a diameter which is larger than the diameter of the interior passage 44 of the wound element 36.

Figure 4:
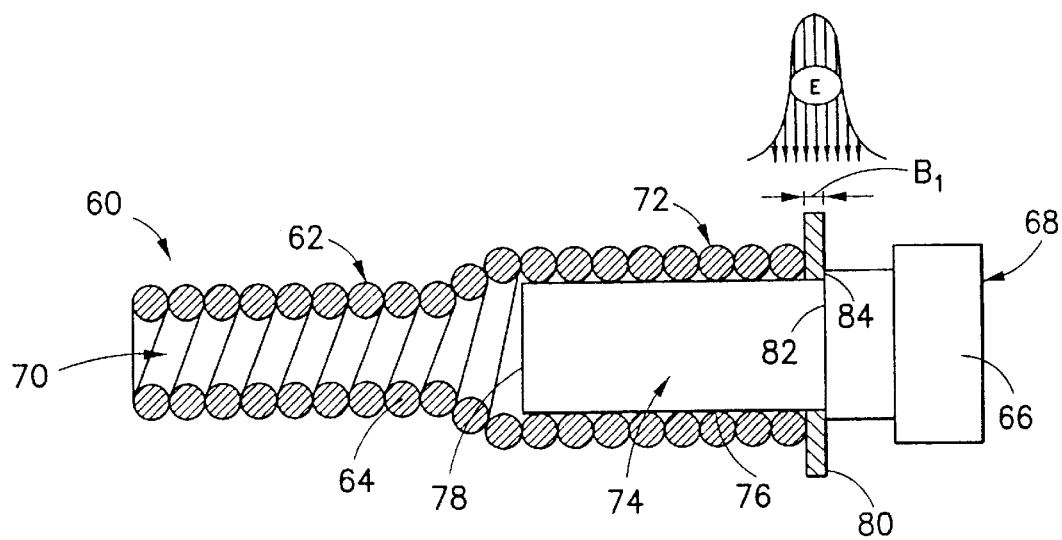
FIG. 4 is a diagrammatic side elevation view, similar to FIG. 2. but illustrating another embodiment of the invention.

For the description, now, of a second embodiment of the invention, turn to FIGS. 3 and 4. In this instance, a weld assembly, or joint, 60 serves to connect a longitudinally extending wound element 62 formed of coiled wire strands 64 and a mating component 66 of a body implantable lead assembly 68. The wound element 62 has an interior passage 70 and an end portion 72. The mating component 66 includes a post 74 for receiving the end portion 72 of the wound element 62. The post 74 has an outer surface 76, a terminal end 78, and a ring member 80 which is a spaced distance from the terminal end 78. The end portion 72 of the wound element 62 is disposed about the post 74, over the terminal end 78, and the ring member 80 is slipped across the outer surface 76 into engagement with a shoulder 82 of the component 66. Thereupon, in a manner to be described, the ring member 80 and the end portion 72 of the wound element 62 are integrally joined together. As in the earlier described embodiment, it is a common practice to construct the weld assembly 60 such that the receiving portion, or post 74, of the component 66 is cylindrical and has a diameter which is larger than the diameter of the interior passage 70 of the wound element 62.

Ends 84 of the coiled wire strands of the wound element 62 are set against the ring member (see FIG. 4). As in the manner of the preceding embodiment utilizing collar 54, the thickness $B_1$ of the ring member 80 is related to the material thermal properties of the wound element 62 and of the component 66 and the diameter of the coiled wire strands 64.

Figure 5:
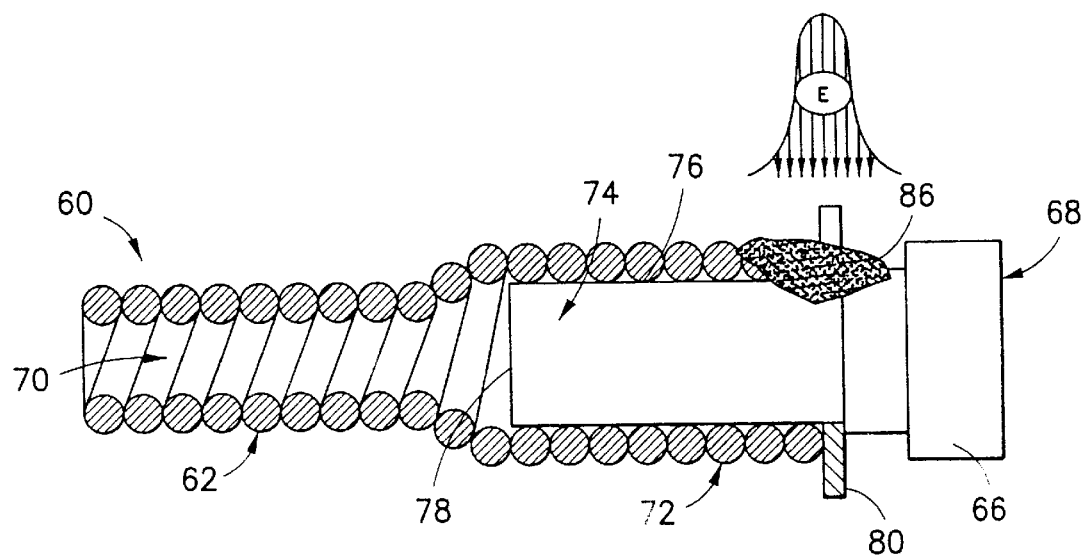
FIG. 5 is a diagrammatic side elevation view illustrating the FIG. 4 embodiment of the invention after the weld has been achieved.

The size of the ring member is selected to provide sufficient melted metal to fill gaps and cavities existing among the wire ends 84, the ring member 80, and the component 66 and thereby produce a positive reinforcing weld joint (see FIG. 5).

A main portion of the energy from a laser beam E is utilized to melt the ring member 80. The peripheral portion of the laser beam heats the shoulder and winding to warm them up, helping the components fuse together. Additional metal for the melted ring member covers the winding and the shoulder of the connector, fusing the components together and filling cavities and gaps between the wires. A specific benefit of this embodiment of the invention resides in the fact that there is no requirement for a specific energy balance between the ring member 80 and the wound element 62. The laser beam E is targeted right in the middle of the ring member 80 and melts it. The weld joint strength is increased due to the weld positive reinforcement which results because the entire ring member becomes a weld nugget after the welding operation.

Further, in this instance, the component 66, wound element 62, and ring member may be made from the same or different materials.

The shape of the ring member can be specifically profiled to control the volume of melted metal around the weld joint.

Figure 6:
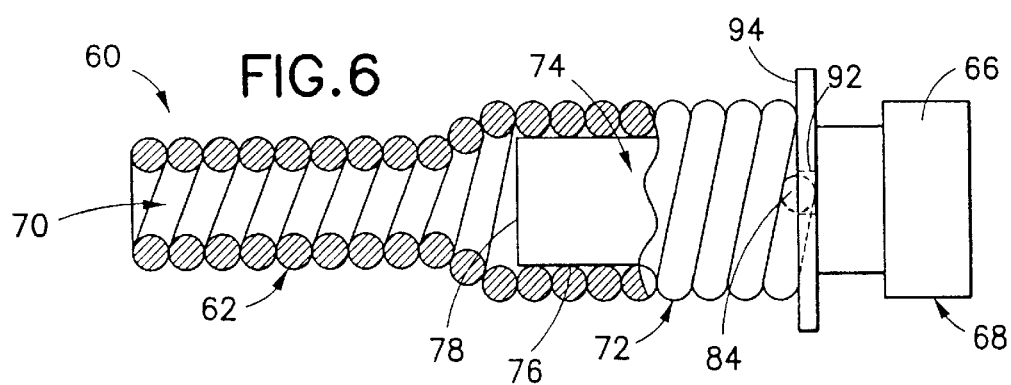
FIG. 6 is a diagrammatic side elevation view, similar to FIG. 5, but illustrating still another embodiment of the invention.
Figure 6A:
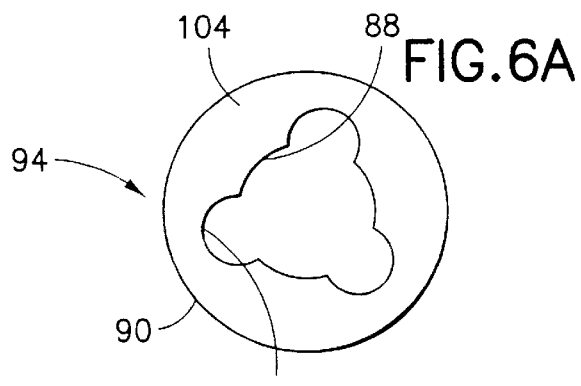
FIG. 6A is a detail elevation view of a modified ring member utilized with the embodiment of FIG. 6.
Figure 7:
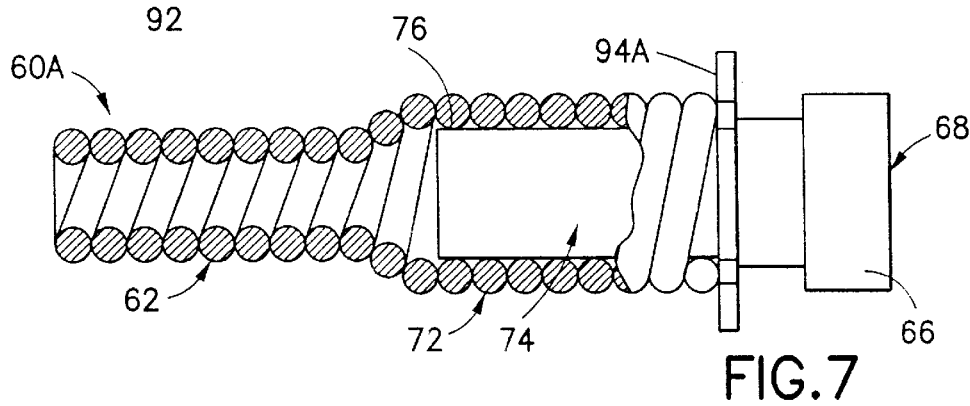
FIG. 7 is a diagrammatic side elevation view, similar to FIG. 6, but illustrating yet another embodiment of the invention.
Figure 7B:
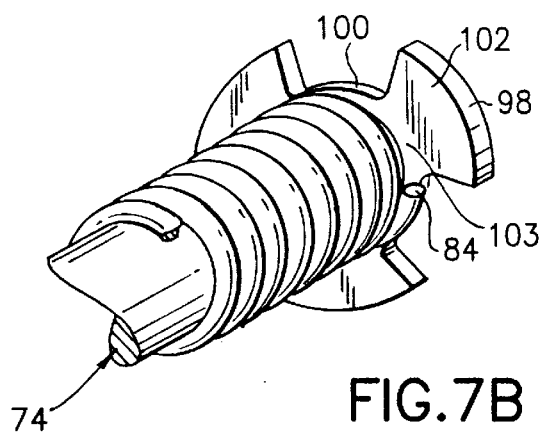
FIG. 7B is a detail perspective view of components illustrated in FIG. 7.
Figure 7A:
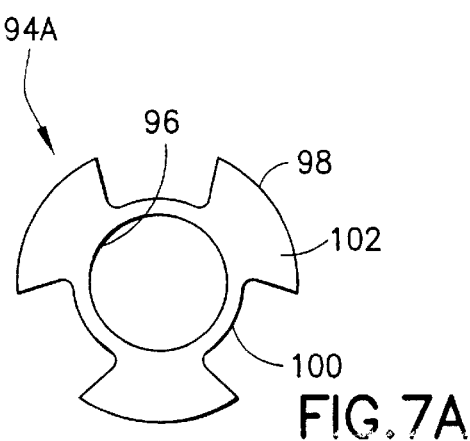
FIG. 7A is a detail elevation view of another modified ring member utilized with the embodiment of FIG. 7.

The illustrations provided in FIGS. 6 and 6A and in FIGS. 7 and 7A, respectively, depict two different examples of the ring member profiles.

In one instance, viewing FIGS. 6 and 6A, a ring member 94 has an inner peripheral surface 88 and an outer peripheral surface 90. The outer peripheral surface 90 may be circular while the inner peripheral surface 88 is profiled with a pocket 92 to control the volume of melted, then fused, metal forming the weld joint. In this regard, as well depicted in FIG. 6A, the pockets 92 also serve to receive the ends 84 of the coiled wire strands of the wound element 62. Indeed, it is common for the wound element 62 to include a coil having a plurality of filars, each terminating at a filar end, the individual filar ends being placed, successively, in the circumferentially spaced pockets 92.

In another instance, viewing FIGS. 7 and 7A, a modified weld assembly 60A includes a modified ring member 94A which has a circular inner peripheral surface 96 for reception on the outer surface 76 of the post 74 and an outer peripheral surface 98. As with the inner peripheral surface 88, the outer peripheral surface 98 is profiled to control the volume of melted, then fused, metal forming the weld joint. Again, in this regard, the outer peripheral surface 98 may include a plurality of circumferentially spaced pockets 100 defining a plurality of circumferentially spaced wings 102. Different from the previously described embodiment, the individual filar ends are placed adjacent an interior cavity 103 (FIG. 7B) defined by the outer surface 76 of the post 74, by the ring member 94A, and by the end portion 72 of the wound element 62. In this latter instance, the wings 102 provide the bulk of the welding material which fills the cavity 103. Of course, with respect to the weld assembly 60, such a cavity is defined by the outer surface of the post, by the ring member 94, and by the end portion of the wound element. In this latter instance, heavier regions 104 of the ring member 94 provide the bulk of the welding material which fills the cavity.

Figure 8:
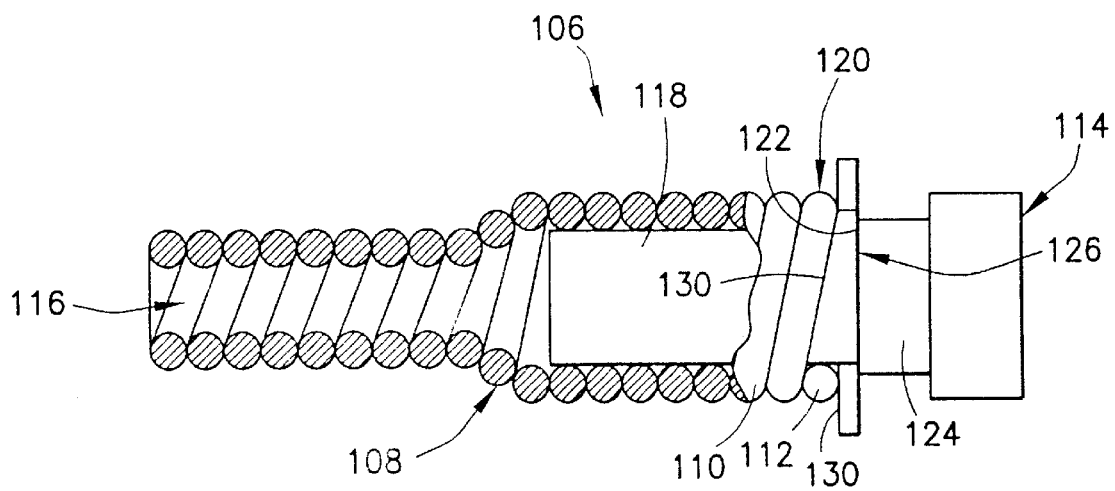
FIG. 8 is a diagrammatic side elevation view illustrating yet another embodiment of the invention.
Figure 9:
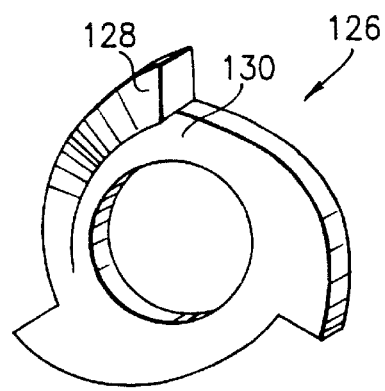
FIG. 9 is a detail perspective view of a component illustrated in FIG. 8.

Yet another embodiment of the invention is illustrated in FIGS. 8 and 9. In this instance, a joint 106 for a body implantable lead assembly serves to connect a longitudinally extending wound element 108 including a coil having at least one filar 110 terminating at a filar end 112 and a mating component 114 of a body implantable lead assembly, the wound element having an interior passage 116. The mating component 114 includes a post 118 for receiving an end portion 120 of the wound element 108. The post 118 extends from a shoulder 122 adjacent a broader portion 124 of the mating component 114, the end portion 120 of the wound element 108 being disposed about the post 118 and being in engagement with the outer surface of the post. The joint 106 further comprises a contoured ring member 126 disposed about the post 118 in engagement with the shoulder 122 and having at least one contoured region 128 on a surface 130 facing the wound element 108. With the end portion 120 of the wound element 108 being in abutting relationship with the ring member 126, the post 118, the ring member, and the end portion 120 of the wound element define a cavity 130. The contoured region 128 on the ring member is so formed that it substantially fills the cavity 130. The post, the ring member, and the end portion of the wound element are integrally joined together by melting of the ring member such that the cavity is filled, or re-filled with molten material which subsequently solidifies, and resulting in the thermal fusion of the post, the ring member and the end portion of the wound element.

Preferably, melting is caused by a laser as in the previous embodiments. Further, in a preferred embodiment, the wound element has a plurality of filars, typically three filars. In this instance, the ring member has a like plurality of contoured regions 128, three being illustrated in FIG. 9.

The following examples are illustrative of the present invention but are not intended in any way to limit the scope of the invention. In each instance, the relationship of formula (1) presented above is applied.

EXAMPLE 1

Assume, that the wire (D=0.004") and the connector are made from the same material MP35N (stainless steel, $a_{wire} = a_{connector} = 6 \times 10^{-6}$ m$^2$/sec). The collar thickness:

$$B = \frac{\sqrt{6 \times 10^{-6}}}{\sqrt{6 \times 10^{-6}}} \times 0.004'' = \frac{2.45}{2.45} \times 0.004'' = 0.004''$$

Thus, the collar thickness B is 0.004", which is equal to the wire diameter D.

EXAMPLE 2

Assume, that the wire is made from MP35N (stainless steel, $a_{wire}=6 \times 10^{-6}$ m$^2$/sec) and its diameter D=0.004", and the connector is made from Pt (platinum, $a_{connector}=25 \times 10^{-6}$ m$^2$/sec):

$$B = \frac{\sqrt{6 \times 10^{-6}}}{\sqrt{25 \times 10^{-6}}} \times 0.004'' = \frac{2.45}{5} \times 0.004'' = 0.00196''$$

Thus, after rounding, the collar thickness B is 0.002", which is two times thinner than the wire diameter D.

EXAMPLE 3

Assume, that the wire is made from Pt (platinum, $a_{connector}=25 \times 10^{-6}$ m$^2$/sec) and its diameter D=004", and the connector is made from MP35N (stainless steel, $a_{wire}=6 \times 10^{-6}$ m$^2$/sec):

$$B = \frac{\sqrt{25 \times 10^{-6}}}{\sqrt{6 \times 10^{-6}}} \times 0.004'' = \frac{5}{2.45} \times 0.004'' = 0.00816''$$

Thus, after rounding, the collar thickness B is 0.008", which is two times thicker than the wire diameter D.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of joining a longitudinally extending wound element and a mating component of a body implantable lead assembly, the wound element having a longitudinally extending interior passage and an end portion adapted to be received by a portion of the mating component, the receiving portion of the mating component being configured to receive the end portion of the wound element, said receiving portion of the mating component having a diameter which is larger than the diameter of the interior passage of the wound element the method comprising the steps of:

(a) placing the end portion of the wound element about the receiving portion of the mating component, wherein the receiving portion of the mating component comprises a post having an outer surface for receiving the end portion of the wound element and wherein the wound element comprises a coil having a plurality of filars, each terminating at a filar end;

(b) placing a ring member about, and in engagement with, the receiving portion of the of the mating component, wherein the ring member has an inner peripheral surface for reception on the outer surface of the post, the inner peripheral surface having a plurality of circumferentially spaced pockets; and (c) joining the ring member, the end portion of the wound element and the receiving portion of the mating component, comprising placing the filar ends of the coil successively in the circumferentially spaced pockets of the inner peripheral surface, and filling a cavity defined by the outer surface of the post, by the inner peripheral surface of the ring member, and by the end portion of the wound element largely from the material of the ring member, targeting a laser beam on the ring member, and thermally fusing the ring member, the end portion of the wound element and the receiving portion of the mating component.

2. The method, as set forth in claim 1, wherein step (c) includes the step of:

(d) thermally fusing the ring member, the end portion of the wound element and the receiving portion of the mating component.

3. The method, as set forth in claim 2, wherein the ring member, the wound element and the mating component are fabricated, selectively, of the same alloy or of dissimilar alloys.

4. The method, as set forth in claim 1:

wherein step (c) is performed by thermally fusing the ring member, the end portion of the wound element and the receiving portion of the mating component to form a weld joint; and wherein the ring member is profiled to control the volume of melted, then fused, metal forming the weld joint.

5. The method, as set forth in claim 4:

wherein the ring member has an inner peripheral surface and an outer peripheral surface; and wherein the inner peripheral surface is profiled to control the volume of melted, then fused, metal forming the weld joint.

6. The method, as set forth in claim 4:

wherein the ring member has an inner peripheral surface and an outer peripheral surface; and wherein the outer peripheral surface is profiled to control the volume of melted, then fused, metal forming the weld joint.

7. A joint connecting a longitudinally extending wound element and a mating component of a body implantable lead assembly, the wound element having an interior passage and an end portion, said interior passage having a diameter, the mating component having a post for receiving the end portion of the wound element, the post having an outer surface, said outer surface of the post having a generally cylindrical configuration with a diameter which is larger than the diameter of the interior passage of the wound element, the end portion of the wound element being disposed about the post and being in engagement with the outer surface thereof, the joint further comprising a ring member disposed about the post, the post, the ring member, and the end portion of the wound element being integrally joined together by melting of the ring member and the resulting thermal fusion of the post, the ring member and the end portion of the wound element, wherein the wound element includes a coil having a plurality of filars each terminating at a filar end, wherein the ring member has an inner peripheral surface for reception on the outer surface of the post, the inner peripheral surface having a plurality of circumferentially spaced pockets for receiving successive filar ends of the coil, and wherein a cavity defined by the outer surface of the post, by the inner peripheral surface of the ring member, and by the end portion of the wound element is filled largely from the material of the ring member.

8. The joint, as set forth in claim 7, wherein the ring member, the wound element and the post are made, selectively, of the same or of dissimilar metallic alloys.

9. A method of joining a longitudinally extending wound element and a mating component of a body implantable lead assembly, the wound element having a longitudinally extending interior passage and an end portion adapted to be received by a portion of the mating component, the receiving portion of the mating component being configured to receive the end portion of the wound element, the method comprising the steps of:

(a) providing the receiving portion of the mating component with an integral collar spaced from a terminal end thereof, the interior passage having a diameter coordinated with the size of the receiving portion of the mating component and the collar, wherein the collar and the wound element are fabricated of dissimilar alloys, wherein the collar has a thickness and the wound element is formed of a coiled wire strand having a diameter, and wherein the thickness of the collar is relatively dimensioned with respect to the diameter of the strand in proportion to the relative thermal diffusivity of the alloy of the collar and of the alloy of the coiled wire strand;

(b) placing the end portion of the wound element about the receiving portion and over the terminal end of the mating component and against the collar; and (c) joining the collar and the end portion of the wound element, comprising thermally fusing the collar and the end portion of the wound element.

10. The method, as set forth in claim 9, wherein step (c) includes the step of:

(d) thermally fusing the collar and the end portion of the wound element.

11. The method, as set forth in claim 10:

wherein the collar and the wound element are fabricated of the same alloy; and wherein the collar has a thickness and the wound element is formed of a coiled wire strand having a diameter substantially equal to the thickness of the collar.

12. The method, as set forth in claim 9, wherein the receiving portion of the mating component is cylindrical and has a diameter which is larger than the diameter of the interior passage of the wound element.

13. A joint connecting a longitudinally extending wound element and a mating component of a body implantable lead assembly, the wound element having an interior passage and an end portion, the mating component including a post for receiving the end portion of the wound element, the post having an outer surface being of a generally cylindrical configuration with a diameter which is larger than the diameter of the interior passage of the wound element, a terminal end, and a collar being a spaced distance from the terminal end, the end portion of the wound element being disposed about the post, over the terminal end, the collar and the end portion of the wound element being integrally joined together by melting of the ring member and the resulting thermal fusion of the post, the ring member and the end portion of the wound element, wherein the collar and the wound element are fabricated of dissimilar alloys, wherein the collar has a thickness and the wound element is formed of a coiled wire strand having a diameter, and wherein the thickness of the collar is relatively dimensioned with respect to the diameter of the strand in proportion to the relative thermal diffusivity of the alloy of the collar and of the alloy of the coiled wire strand.

14. The joint, as set forth in claim 13:

wherein the collar and the wound element are fabricated of the same alloy; and wherein the collar has a thickness and the wound element is formed of a coiled wire strand having a diameter substantially equal to the thickness of the collar.

15. The joint as set forth in claim 13, wherein the contoured ring member has a plurality of contoured regions at circumferentially spaced locations on the surface facing the wound element, the plurality of contoured regions being equal in number to the number of filars of the wound element.

16. A joint connecting a longitudinally extending wound element including a coil having at least one filar terminating at a filar end, and a mating component of a body implantable lead assembly, the wound element having an interior passage, the mating component including a post for receiving the end portion of the wound element, the post having an outer surface and extending from a shoulder adjacent a broader portion of the mating component, the end portion of the wound element being disposed about the post and being in engagement with the outer surface thereof, the joint further comprising a contoured ring member disposed about the post in engagement with the shoulder and having at least one contoured region on a surface facing the wound element, the interior passage having a diameter coordinated with the size of the post and the ring member, the end portion of the wound element being in abutting relationship with the ring member, the post, the ring member, and the end portion of the wound element defining a cavity, the contoured region on the ring member substantially filling the cavity, the post, the ring member, and the end portion of the wound element being integrally joined together by melting of the ring member, filling the cavity and resulting in the thermal fusion of the post, the ring member and the end portion of the wound element, wherein the ring member has a plurality of contoured regions at circumferentially spaced locations on the surface facing the wound element, the plurality of contoured regions being equal in number to the number of filars of the wound element.

17. A joint connecting a longitudinally extending wound element and a mating component of a body implantable lead assembly, the wound element having an interior passage and an end portion, the mating component including a post for receiving the end portion of the wound element, the post having an outer surface being of a generally cylindrical configuration with a diameter which is larger than the diameter of the interior passage of the wound element, a terminal end, and a collar being a spaced distance from the terminal end, the end portion of the wound element being disposed about the post, over the terminal end, the collar and the end portion of the wound element being integrally joined together by melting of the ring member and the resulting thermal fusion of the post, the ring member and the end portion of the wound element, wherein the wound element includes a coil having a plurality of filars, each terminating at a filar end, and wherein the ring member has a peripheral surface for reception on the outer surface of the post, the peripheral surface having a plurality of circumferentially spaced pockets for receiving successive filar ends of the coil.

* * * * *